(12) United States Patent
Pulkkinen et al.

(10) Patent No.: US 7,805,186 B2
(45) Date of Patent: Sep. 28, 2010

(54) SYSTEM FOR MONITORING AND PREDICTING PHYSIOLOGICAL STATE UNDER PHYSICAL EXERCISE

(75) Inventors: Aki Pulkkinen, Palokka (FI); Erkkl Saarikoski, Espoo (FI)

(73) Assignee: Firstbeat Technologies Oy, Jyvaskyla (FI)

( * ) Notice: Subject to any disclaimer, the term of this patent is extended or adjusted under 35 U.S.C. 154(b) by 496 days.

(21) Appl. No.: 11/154,444

(22) Filed: Jun. 16, 2005

(65) Prior Publication Data
US 2006/0004265 A1   Jan. 5, 2006

(30) Foreign Application Priority Data
Jun. 16, 2004   (FI)   ................. 20040240 U (51) Int. Cl.
*A61B 5/04*   (2006.01)
(52) U.S. Cl. .......................................... 600/520; 482/8
(58) Field of Classification Search ................. 600/520; 482/4–9, 901, 902
See application file for complete search history.

(56) References Cited
U.S. PATENT DOCUMENTS

| | | | | |
|---|---|---|---|---|
| 4,278,095 A * | 7/1981 | Lapeyre | ...................... | 600/520 |
| 4,566,461 A * | 1/1986 | Lubell et al. | ................. | 600/520 |
| 4,883,063 A * | 11/1989 | Bernard et al. | ............... | 600/519 |
| 5,297,558 A * | 3/1994 | Acorn et al. | ................. | 600/520 |
| 5,318,487 A * | 6/1994 | Golen et al. | .................... | 482/5 |
| 5,403,252 A * | 4/1995 | Leon et al. | ....................... | 482/5 |
| 6,605,044 B2 * | 8/2003 | Birnbaum | .................... | 600/500 |

FOREIGN PATENT DOCUMENTS

WO   WO 2004016173 A1 *   2/2004

* cited by examiner

*Primary Examiner*—Scott M Getzow
*Assistant Examiner*—Joseph M Dietrich
(74) *Attorney, Agent, or Firm*—Fildes & Outland, P.C.

(57) ABSTRACT

The invention relates to a system for monitoring a cumulative physiological state and for predicting a target state under physical exercise, which system includes means for measuring a variable depicting the intensity of the exercise and for registering it relative to time, the control unit consisting of a user-interface device, which includes an input device and output device. Software means calculate the current value of the said cumulative physiological variable while second software means calculate the value of a selected output variable, which output variable is one of the following three variables: target state, future intensity, or duration of future exercise, the two other variables being given as initial variables.

10 Claims, 11 Drawing Sheets

Fig. 13

SYSTEM FOR MONITORING AND PREDICTING PHYSIOLOGICAL STATE UNDER PHYSICAL EXERCISE

BACKGROUND TO THE INVENTION

1. Scope of the Invention

The present invention relates to a system for monitoring a cumulative physiological state and for predicting a target state under physical exercise, which system includes means for measuring a variable depicting the intensity of the exercise and for registering it relative to time, the control unit consisting of a user-interface device, which includes an input device and output device. In the control unit, there are software means for performing calculations.

The term physiological target state of the user refers to a state achieved by a selected intensity of exercise and a selected duration of the exercise.

2. Description of the Prior Art

A conventional exercisers's and sportsperson's heart-rate meter consists of a heart-rate transmitter component and an operating device. The heart-rate transmitter is usually an ECG sensor and radio transmitter, or some other device for transferring data, secured on top of the chest. The control unit is often of a model that is attached to wrist, in which there is a receiver, keypad, display, and processor for performing the desired functions. Another general model consists of an operating device connected to an exercise machine. Such exercise machines include stationary cycles, rowing machines, cross-trainers, steppers, etc. Instead of heart-rate, some other variable depicting physical activity can be used. Exercise machines permit the physical power of a person to be determined precisely, through external power.

Application publication U.S. 2003/0028116 'Caloric Exercise Monitor' discloses one heart-rate meter monitoring caloric consumption. In this case, the user sets a specific number of calories/weight reduction as a target prior to training. During training, the consumption of calories is calculated with the aid of heart rate and the user is shown the number of calories consumed, the time taken to reach the target, and the number of calories remaining before the target. However, the consumption of calories does not depict a physiological state. The amount of calorie consumption is poorly suited physiologically as a correct measure of physical training. The target is approached the whole time, despite the intensity of the exercise. In fact, on the basis of calorie consumption a user has no way of knowing whether the training is effective relative to their personal state.

U.S. Pat. No. 6,405,077 'Method in Connection with Personal Non-Invasive Heart-Rate Measuring Arrangement with Alarm' discloses another heat-rate monitor for directing training. In order to control the level of training, specific heart-rate limits (lower and upper limits) are set for the heart-rate monitor, between which the heart rate should remain. If the heart rate rises/drops away from the target range, the monitor gives an alarm. In interval-type training, several heart-rate limits can be set, which are activated at a set time. In U.S. Pat. No. 6,405,077, the intensity (heart-rate level) of the exercise is used as the target state, so that the real effect of the training (e.g. development of $VO_2max$) can not be predicted relative to time.

U.S. publication 6411841 'Human-Related Measuring Assessment' discloses a training device, in which the lactate content of the blood is calculated with the aid of the heart-rate, power, or speed, in order to depict the intensity of exercise.

U.S. Pat. No. 6,687,535 'Controlling of Fitness Exercise' discloses a method, in which the lactate content of the blood is measured with the aid of the heart rate from exercise. After loading, the optimal heart-rate level for the final warm-up is found (exploiting the variation in heart rate), by means of which the removal of lactate would be as efficient as possible. The monitor shows a real-time assessment of the lactate content, so that the user can end the warm-up, once the lactate has dropped to the desired level. As such, lactate depicts best the intensity of exercise and thus poorly the cumulatively accumulated exercise, so that a specific lactate level is not a good physiological target state.

International patent publication WO 2004/016173 discloses widely a method for monitoring physical state during exercise. The essential feature of the method is to create a cumulative exercise index that depicts the cumulative exercise load at each moment and, in addition, the corresponding necessary recovery time, without the duration of the exercise being require as a variable, but by including it in the current index at each moment. The most important factor in the BFI index that has been developed is the 'upslope component', which sums the exercise on a scale that implement physiological recovery using all the values. This is scaled preferably numerically to an EPOC value, which can be described simply as the body's oxygen deficiency. In the publication, the prediction of the physiological state is given quite little attention, even though it is quite central to the user. In connection with FIGS. 9 and 10 of the aforementioned WO publication, the use of the EPOC value as a physiological meter is explained and an example is presented of selected training-effect areas. The publication discloses neither a suitable user interface for exploiting the cumulative exercise index, nor a method for predicting the target state.

SUMMARY OF THE INVENTION

The present invention is intended to create an economical and practical system for monitoring a cumulative physiological state and for predicting a target state under physical exercise. The system can be used to aim more easily than before at a real training effect in exercise.

The system includes
means for measuring a variable that depicts the intensity of exercise and for registering it relative to time, and
means for measuring intensity and time, connected to an control unit, consisting of
  a user-interface device, consisting of an input device for selecting the output variable and for entering the values of the initial variables, and an output device for displaying the output variable,
  first software means for calculating the current value of the said cumulative physiological variable, with the aid of the measured intensity of exercise and the preceding value,
  second software means for calculating the value of an output variable, the output variable being one of the following three variables: target state, intensity of future exercise, or duration of future exercise; the two other variables being given as the said initial variables, and in which the system is arranged to calculate and display the value of the output variable using the input device, essentially in real time and continuously.

In the method according to the invention:
a) a variable depicting the intensity of exercise is measured and is registered relative to time, and
b) the current value of the said cumulative physiological variable is calculated with the aid of the intensity of the exercise with the aid of the preceding cumulative value, c) the mutual relationship of the future target state, the future intensity, and the duration of the future exercise is calculated in such a way that one output variable is selected from these, the two other variables being the initial variables with selected parameters, d) the selected output is displayed essentially in real time, and e) a return is made to stage a).

The calculation of the mutual relationship of the target state, the intensity of exercise, and the duration of exercise permits predictive information, in which one physiological variable can be calculated, if two other variables are known, in addition to the present value of the first physiological variable. The mutual relationship is advantageously obtained by simulating the cumulative variable at a selected intensity, up to the target state, in which case the predicted duration will be returned. The prediction obtained is compared with the set time, on the basis of which the intensity is corrected and recalculated, until the initial parameters are realized. Correspondingly, it is possible to vary the target state and calculate the predicted duration, which is used to correct the value of the target state. The mutual relationship is thus obtained by simulating the cumulative variable and using the selected output parameters, the result of which simulation being a correction to the value of the output parameter. Simulation is continued until the initial parameters are realized.

The display device should show at least the output variable in real time and essentially continuously, in order to complete the exercise as planned. In this case, the term 'continuously' means sufficiently often, according to the training. In one embodiment, the operating device and its display are arranged to show the development of the exercise graphically as a function of time. The time need not be registered separately, if the measurements are registered at regular intervals (known $\Delta t$).

The input function of the operating device can be based on a keypad, speech recognition, or similar. The output device is usually a display, but sound messages, particularly a voice synthesizer, can also be used. The sound or voice message can be given, for example, only when a deviation from the 'route' to the planned target state occurs.

The means for measuring a variable depicting the intensity of exercise consist of a measuring device for measuring one or more variables from the following group: external power (from an exercise device), motion (acceleration sensor), energy consumption, heart rate, oxygen consumption (flow meter+$O_2$/$CO_2$ sensor), respiration rate (pressure sensor), or heat flow on the surface of the skin (thermometer).

BRIEF DESCRIPTION OF THE DRAWINGS

In the following, the invention is examined with reference to the accompanying drawings, which show some applications of the system according to the invention.

FIGS. 5c and 5d show displays of the user interface at the point 'SPLIT' of FIG. 5a.

FIG. 6c shows a display of the user interface at the point 'SPLIT' of FIG. 6a.

DESCRIPTION OF PREFERRED EMBODIMENTS

Figure 1:
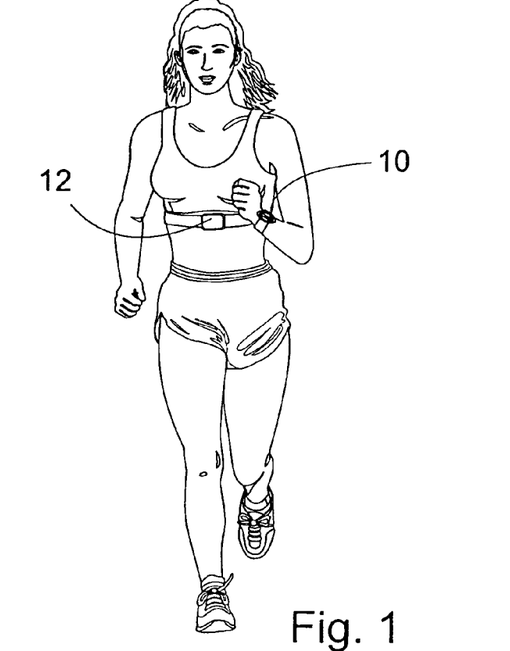
FIG. 1 shows the main components of the system, worn on the user.

The system according to the invention can be applied in many kinds of device. FIG. 1 shows an operating device 10 (wristop device) worn on the wrist and used by a conventional fitness enthusiast or sportsperson. A heart-rate transmitter 12 is attached by a suitable band on the chest of the user. The transmitter 12 is in radio contact with the receiver of the operating device 10. The invention is also suitable for use in connection with exercise devices, such as a stationary cycle or rowing machine. The invention can also be applied in connection with a mobile telephone (mobile station, or more generally a PDA device), for example, over a Bluetooth connection or simply over a wire connection. The application program is then implemented in the operating system (e.g., Symbian/Nokia® Series 60 or Windows CE). Generally the device is primarily personal, either fully portable or else connected to the exercise device being used. In the device, there is a microprocessor 32 (CPU), a memory 33 (e.g., ROM), and I/O means, such as a display 15 and a keypad 18. In addition, in the device there is a connector for a heart-rate monitor 12 or some other sensor that measures the intensity of exercise. In the wristop device itself, there can be, for example, a thermometer to depict the heat flow from the skin.

Figure 13:
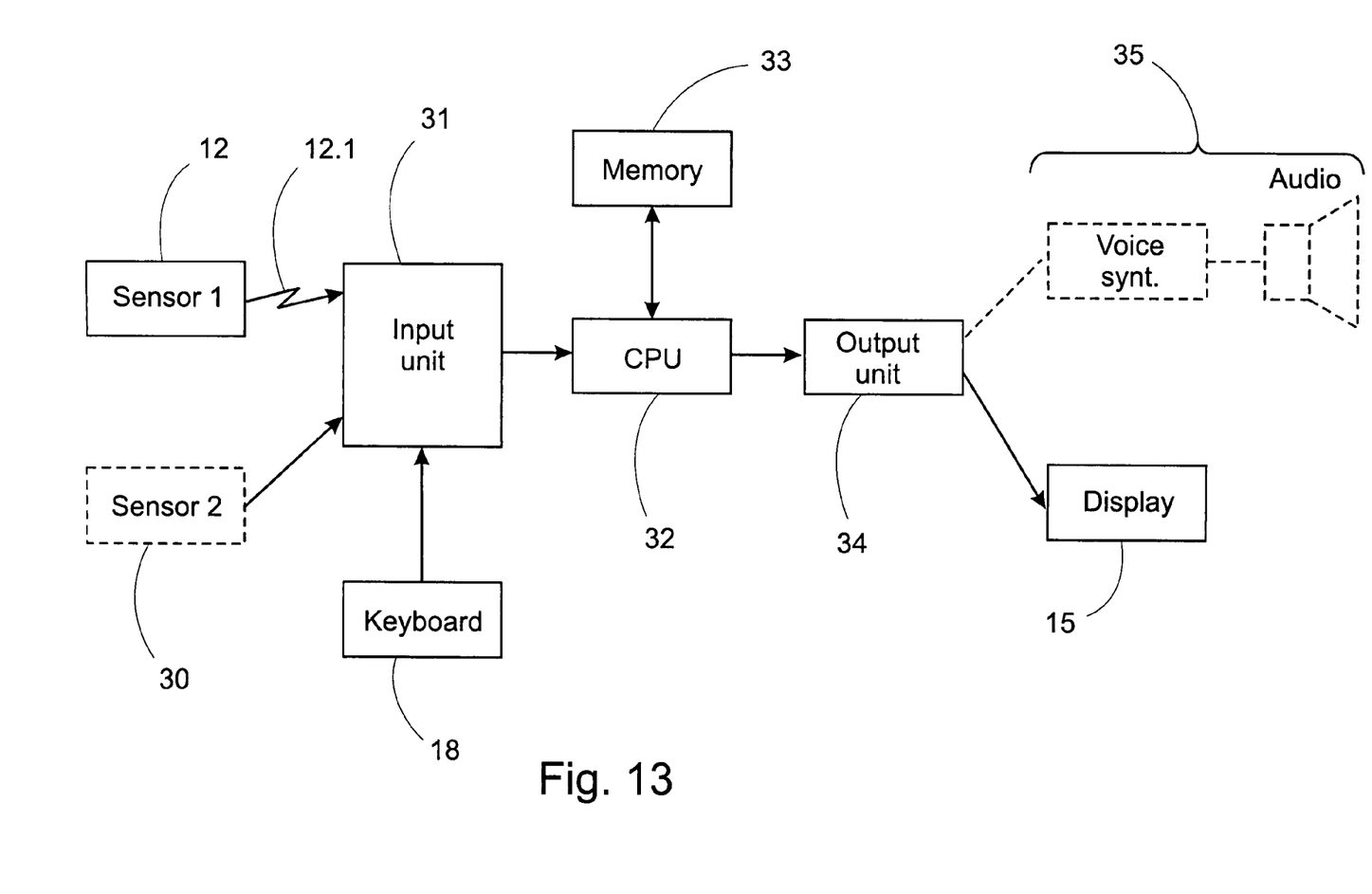
FIG. 13 shows a block diagram of the system of the embodiment according to the invention.

According to FIG. 13, the system has as an input device a sensor 12 (e.g., a heart-rate monitor) measuring intensity. In addition to heart-rate measurement, it is also possible to use, for example, motion measurement (a second sensor 30), as shown by the broken line. In addition, in most applications, personal parameters are entered before using the device for the first time. The input data is led to the CPU 32 through an input unit 31. There are software means in the memory 33 (ROM/RAM). From the CPU the data is led through the output unit 34 to an output device, which is, for example, a display 15. In addition or alternatively, it is possible to use a voice-synthesizer 35 with an audio-terminal device, to present the output variable (and even menus).

Figure 2:
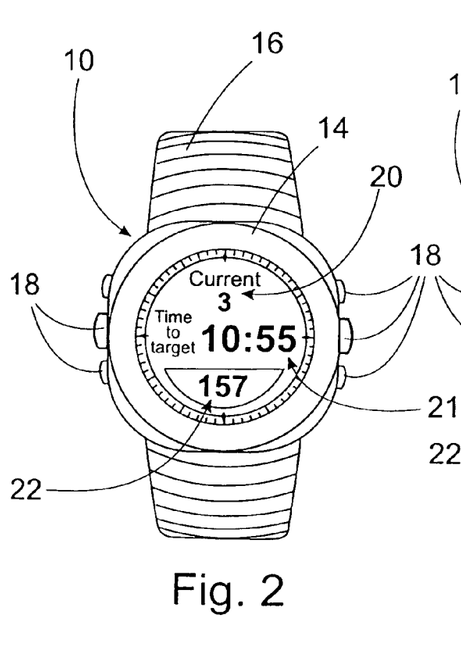
FIG. 2 shows a first application of the user interface.
Figure 3:
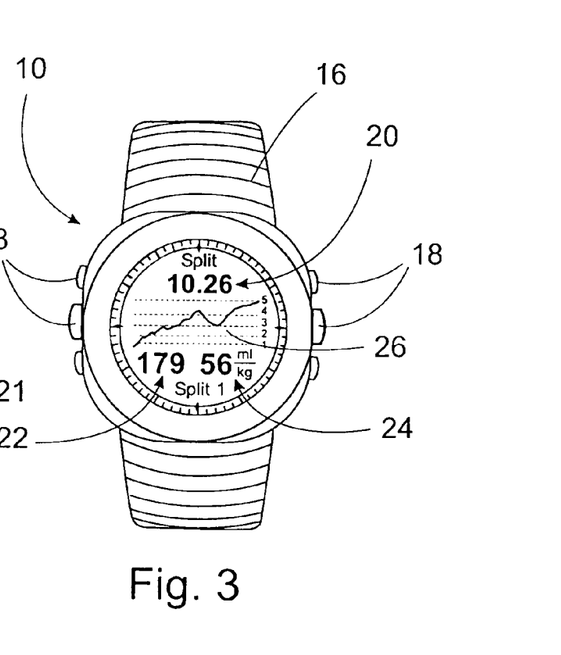
FIG. 3 shows an additional application of the user interface to show a graphical descriptor.

FIGS. 2 and 3 show the operation of the wristop operating device in greater detail. The operating device mainly corresponds to known highly developed operating devices of heart-rate monitors, in which there is a 'watch component' 14 held on the wrist by a strap 16, in the manner of a wristwatch. In it, there is a display device 15, keys 18, the said heart-rate data receiver, and the processor component. Entry of the initial data and the target state takes place using the keys, using some logic that is, as such, known.

In the embodiment of FIG. 2, there are several numerical display fields (in either one or more physical fields) in the display device 15. It is essential that the system is able to calculate continuously the mutual relationships of the physiological exercise state continuously, the intensity of future exercise, and the duration of the future exercise, and to create predictive information. One variable of the three can be calculated, if the other two are known. Naturally, the system is given some personal parameters. The display device should show at least the output variable, preferably all three as in the embodiment of FIG. 2. In the state field 20, there is a preset target state, in the time field 21, there is the time calculated to achieve the target state at the same intensity of exercise, which is shown by the heart-rate value of the heart-rate field 22.

In the operating mode of FIG. 3, the operating device and its display are arranged to show the development of exercise graphically, as a function of time. For this purpose there is a graphical display field 26 in the display component. In this mode, an additional field 24 is shown, which displays the momentary EPOC value.

The training effect can be determined as follows: in this document the term Training Effect refers to an invention, which evaluates the development of the maximal aerobic fitness, in particular the development of maximal oxygen uptake and fatigue resistance capability, on the basis of the estimated EPOC. EPOC can be estimated with the aid of heart rate or similar measure.

The scientific background to EPOC and the training effect: It can be seen from the literature on physical training that the harder the training has been, the more the homeostasis of the body is disturbed. The more that the homeostasis can be disturbed, the greater the adaptations that can be created in the body and the improvements in physical condition that derive from the adaptations.

EPOC measures the degree to which the body's homeostasis has been disturbed (e.g., Brooks & Fahey, 1984). Thus EPOC also measures the degree of improvement in condition that takes place after training. The greater the EPOC the greater the improvements in physical condition that take place after training (=Training Effect).

The degree of improvement in physical condition can be estimates with the aid of the EPOC produced by the training. The EPOC that has accumulated during training can indeed be divided into five Training Effect classes:

1 No significant,

2 Maintaining Training Effect,

3 Improving Training Effect,

4 Highly Improving Training Effect,

5 Temporary overload.

On the basis of the literature it can thus be stated that the greater the EPOC the greater the training effect. The boundaries of the training effect classes are defined on the basis of the training literature and on exercise recommendations (e.g., American College of Sports Medicine (ACSM) 2001: Rusko 2003), FIG. 12 The EPOC boundaries of the training effect classes are defined separately in ten (10) separate levels of activity, starting from no training at all and ending with a top-level endurance sportsperson; a higher EPOC is required from someone with a higher level of activity for the achievement of a specific training effect, FIG. 12. This training effect is very suitable as the said cumulative variable, because it takes the personal level of activity into account.

Operation of the User Interface

1) In one embodiment of the system, the following data are entered:

Background Data age, height, weight, activity class, sex, (smoking)—the requirement depends on which variables are desired in the output:

EPOC

Figure 11:
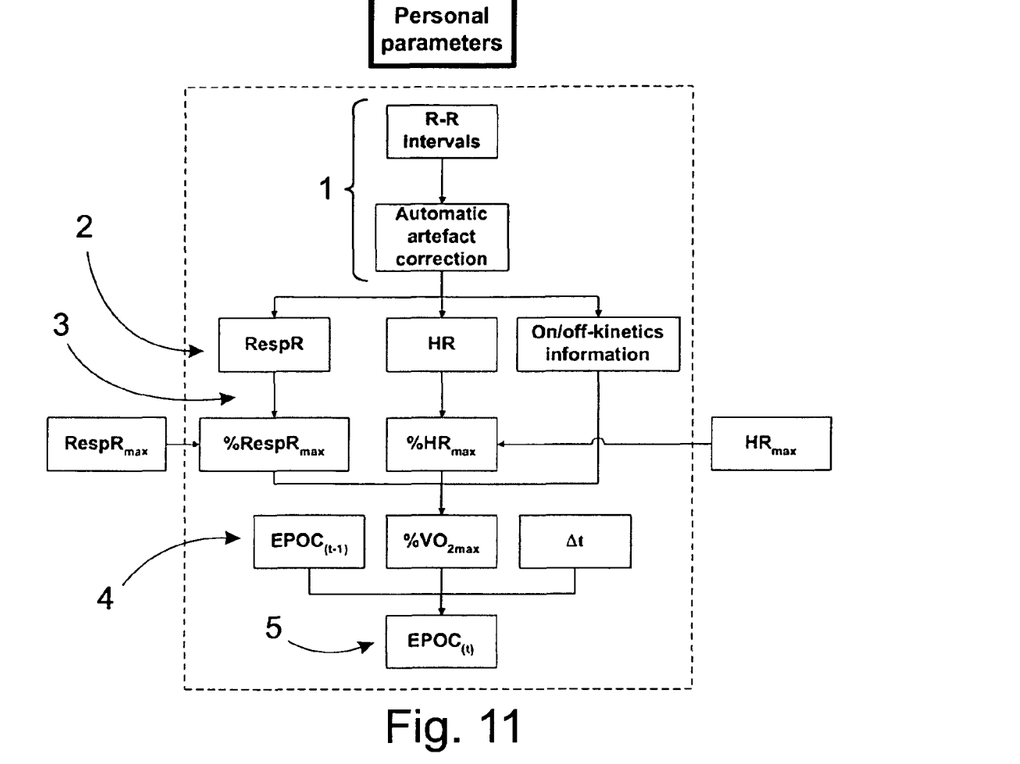
FIG. 11 shows a block diagram of the EPOC calculation.

In the internal calculation of the EPOC, % $VO_{2max}$ (proportion used of person's maximal oxygen uptake) data are required. The calculation of this requires the maximum heart rate (age) and the maximum respiration rate (age, height, weight, smoking). If necessary, smoking can be given the default value zero. FIG. 11 shows a block diagram for the calculation of % $VO_{2max}$ and from that the EPOC value. Maximum heart rate (HRmax) and maximum respiration rate (RespRmax) are entered as personal parameters.

Description of EPOC Estimation (FIG. 11):

1. The RR intervals are recorded beat by beat. After recording, the artefacts (errors) are corrected automatically from the heat-rate data.

2. The heart (beats/minute) (HR) and the respiration rate (breaths/minute) and the data on the loading stage (rising/falling/even oxygen consumption) (=on/off kinetics information) are extracted from the corrected heat-rate data.

3. The measured heart rate and the respiration rate are proportioned to the person's maximum heat rate (HRmax) and maximum respiration rate (RespRmax), which maximum values are either entered ready into the program, or else the program predicts them on the basis of the person's background information. The output obtained in the percentage share of the maximum heart rate (HRmax) and maximum respiration rate (RespRmax).

4. With the aid of the % HRmax and % RespRmax values (the user provides these parameters) and the loading stage data (on/off kinetics information), the intensity is estimated, which is stated as the used percentage share of the maximum oxygen consumption (% $VO_2$max).

5. The current EPOC (EPOC(t)) is finally estimated utilizing the data of the preceding measurement moment's EPOC (EPOC(t−1)), the time that has passed between the present measurement moment and the preceding measurement moment ($\Delta t$) and the intensity (% $VO_2$max) between the preceding and present measurement moments.

Individual Training Effect Ranges

Figure 12:
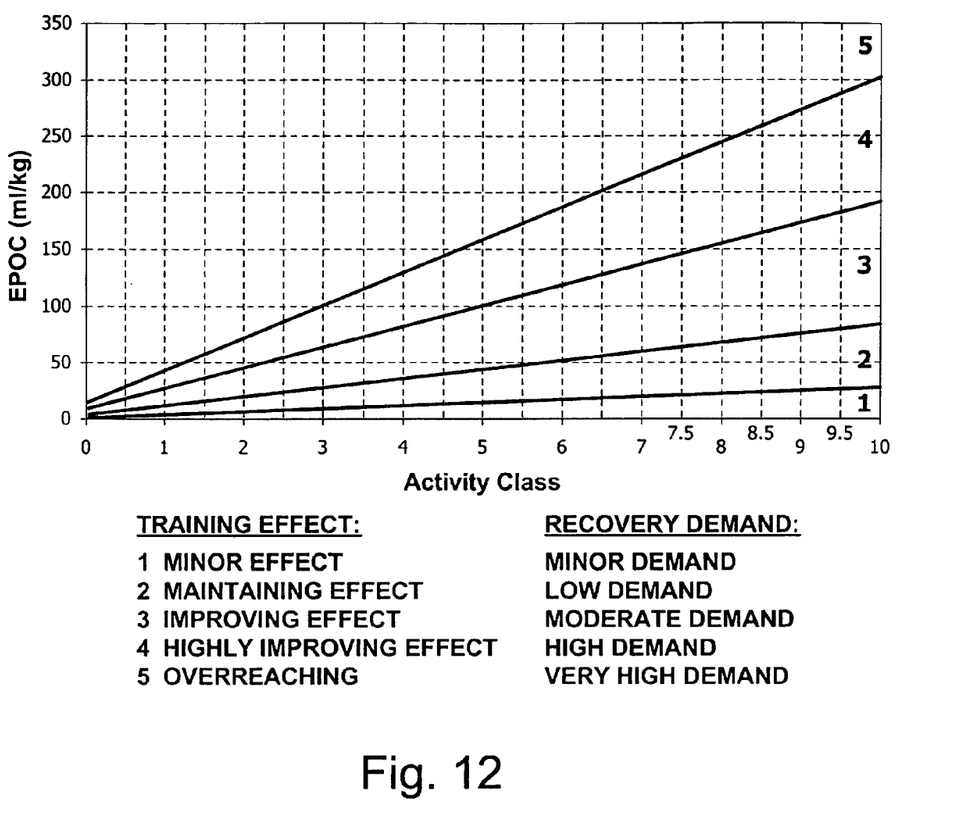
FIG. 12 shows training effect boundaries as functions of the degree of activity.

In order to determine the training effect ranges, the $VO_2$max is required as an absolute value, for which age, height, weight (BMI), sex, activity class or simply the user's activity class are required. In FIG. 12, the range limits of the training effect are shown as a function of the activity class.

2) Example Modes of the System

In the operating device, the following principal operating states can be selected:

1. mode: free operation—all the variables are monitored, for instance, accumulated EPOC, training effect achieved, time to achieving the following training effect at present intensity, recovery time, 2. mode: desired training effect—calculate and display the time required to achieve the selected target, if the intensity of the exercise remains the same, 3. mode: desired training effect and the available time—the target and maximum time are selected and the necessary change in intensity for achieving the target within the selected time is displayed, 4. mode: precise EPOC value—target is selected directly as an EPOC value—the time for achieving the target at the present intensity is calculated and displayed, 5. mode: predictive training result—calculates what EPOC or training-effect will result at the present intensity without the set time.

In the various modes, the EPOC value is accumulated as the training progresses. In one application, a specific EPOC value is set as the initial value, if monitoring is started in the middle of training.

In each principal mode, there are possible sub-modes.

In one embodiment of the operating device there are two display states, the information in one relating to loading and in the other to recovery.

FIGS. 4a-4d show the invention through display modes, in which the display can be envisaged as relating to an exercise device. The input device is typically a special keypad.

Figure 4A:
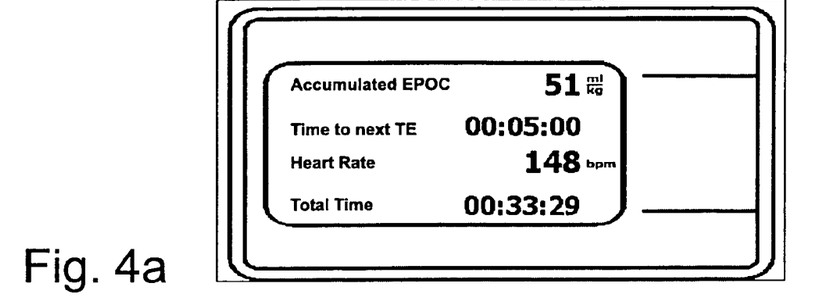
FIGS. 4a-4d show displays of the exercise device in various modes.

FIG. 4a shows the aforementioned 1. mode (free operation). The cumulative EPOC value, the heart-rate data depicting the intensity of the exercise are the initial data of the calculation. The predefined training effect ranges define the steps (1-5, see, for instance, the WO publication and FIG. 12), to which the momentary EPOC value is compared. The output data shown is the time to the next limit. In addition, in this case the total time of the training is shown.

Figure 4B:
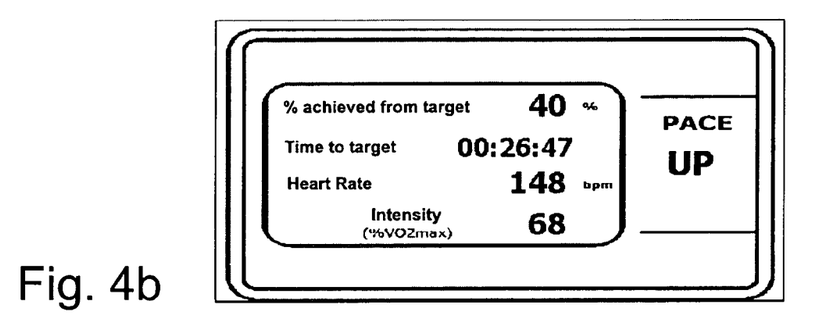

FIG. 4b shows the operation of the system in mode 4. The precise EPOC value is entered as the target, in which case the intensity at each moment is used to calculate the time required to achieve the target. This amount of time is shown together with the achieved percentage target value, the momentary heart rate, and the momentary power value.

Figure 4C:
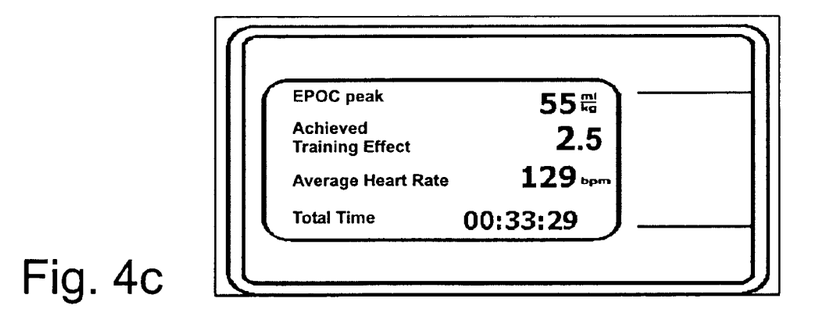
Figure 4D:
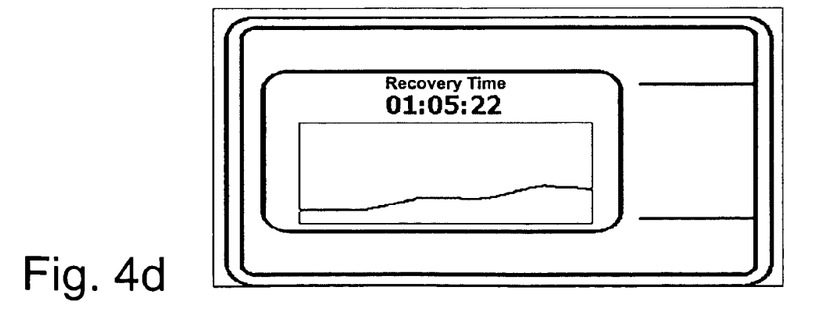

FIGS. 4c and 4d show the results of the training. In 4c numerically and in 4d graphically. The physiological training effect is best depicted by the peak EPOC value. The display of FIG. 4d also shows the time required for complete recovery.

Training is commenced conventionally by starting the stop watch. From this moment on, information relating to the progress of the training is given on the exercise display. The recovery display can also be used to check the recovery requirement set by the training up to that point. Once the training has finished, the measurement is stopped quite normally by stopping the stop watch. The data of the recovery display do not stop, instead data relating to recovery continues to be given. If the heart-rate measurement continues (the user does not remove the band), data derived from the heart rate is used as the intensity level. If the user removes the heart-rate band, complete recovery is assumed (about rest level intensity). In the recovery state, achievement of full recovery is notified. In the recovery stage, the target state corresponds to the EPOC value 0 and the output variable the time required for the recovery when the intensity is at resting level.

If the user starts a second training session before the EPOC of the preceding training session has burnt off, the training starts from this EPOC level. However, the user has the possibility to reset the EPOC (interference signals, etc.). The EPOC then remains in the memory for as long as it exists, or for as long as it is wished to retain it in the memory.

In the training planning state, the user can plan their training program using a day-specific EPOC dose. Seven days are always set on the display, the middle one of which is the current day. The EPOC dose planned for the coming days would appear as empty columns while the EPOC on the previous days would appear darkened in the columns. If the target has not been reached, there is empty space in the columns, if it has be exceeded, there will be a line at the target and the darkening will continue over the line. The time line of the days can be moved laterally. It is possible for this to contain the days of weeks or even months.

In more advanced models, there could also be a functionality for monitoring recovery, inside the training function, in which; for example, interval training would be directed (or in the lightest form monitored) by the EPOC level during the recovery periods. Depending on the aim of the training, the user can define that the EPOC should recover during an interval to less than a specific level, or that the EPOC should not recover by more than a specific amount. In certain types of training, it is essential that a full recovery is made before the next exertion, in order to make, for example, a good technical performance, or so that it will load the energy producing system correctly. In certain training, a sufficiently great loading should be achieved, but in order to achieve it small recovery periods are required, so that the work power of the exertions will remain sufficiently high and the total duration of the training can be extended.

In a simplified models there is only a single display state, which operates like a conventional stop-watch model.

Operating Example

Training

On the first use, the user sets their own personal background values in the clock in place of the default values. The user sets the target as a developing training effect (3). The user sets the time target at 45 minutes, as there is no more time available. When the training starts, the user starts the timing. This time, the user does not perform an initial warm-up, but only decides to take the first 5 minutes of the training more easily. Due to this, in the training display the blinking arrow image points upwards, because at this rate the training effect cannot be achieved within the set time. After the first five minutes, only a small part of the training target has been achieved due to the low intensity, which can be seen at a glance from the sector surrounding the watch face. At this intensity, achieving the training effect will take 1 h 15 min. The display states that at the moment the training effect is 1 (no significant training effect). At the moment, the EPOC is 9 ml/kg. From the recovery display, the user notices that at the moment the recovery requirement is not very significant, full recovery will be achieved with 7 minutes rest.

Now the user clearly increases the intensity of the training. At this moment, the intensity corresponds to 65% $VO_2$max while as a heart rate this is 160 times/min for them. At this exertion, the training effect 3 will be reached within the target time. At this exertion, the time to reach the training-effect area 2 is only 8 minutes. At the 25-minute point in the training, half of the target has been achieved, at that moment the EPOC is 25 ml/kg. The recovery requirement too is greater—60 minutes to full recovery.

When 44 minutes of total time has passed, the watch notifies that the target has been achieved. There are still about 500 metres to before reaching home, so the user decides to use this for a final cool-down. When they reach home, the user takes the band off their chest. From the recovery state display, the user sees the progress of recovery; at that moment there is 1 hour 45 minutes to full recovery, now that 45 minutes have passed since the end of the training session; at its greatest the recovery requirement was 3 hours 15 minutes before the final wind-down.

The user decides to perform another training session. 2 hours have passed since the end of the previous session. From the recovery display the user sees that they have not yet fully recovered: according to the descriptor, there is still an EPOC of 9 ml/kg remaining and there would still be 10 minutes to full recovery. Nevertheless, the user starts a new training session by starting the stop watch in the training state. Recovery is not complete and there is still EPOC remaining from the previous session, which can be felt slightly in the body.

Training-Session Planning and Monitoring:

The user moves to the training-session planning and monitoring state. The display has the sessions of the three preceding days, the present day, and the three following days. For the following days, the user decides to set the target as training effects of 3, 5, and 4. The targets could also be set directly at EPOC values, but the user still does not know their own precise EPOC values for the target level. On the previous days, the targets have been reached well, which can be easily seen from the fact that the columns at these days are almost full or even over the target. Today is an easy day in the programme, the planned column is low. The user browses the training sessions of the past two weeks by scrolling backwards through the days shown on the display. The sessions have clearly become harder from the first days, now it is even possible to train without the muscles becoming sore at once.

Changing the training target during the session, if it feels difficult or it is wished to train more.

Reaching the target with the ring: 1) percentage achievement, 2) achievement in the scale, when the numbers on the ring come from the training effect. In the scale it is necessary to consider when the set the training effects to come linearly for users of different condition, in which case the effect ranges can be set to be fixed.

In a split display, a 15-minute curve appears on the display according to a break (the final quarter hour), in which the split point is in the middle. It is also possible to scroll freely.

In the recovery display, there is also the final quarter hour and a possibility to scroll freely.

The operation according to the example can be advantageously extended in time to also concern the target exercise dose for one day, week, or month. In addition, the target limits can be defined on the basis of health related fitness or other criteria that are important to the user. These include weight management and stress prevention.

In one embodiment of the device, the user downloads wirelessly to their own device an EPOC profile or target make or prepared by another user or coach. During operation, the user can compare the EPOC of their own training or implementation of the profile of the training effect relative to the training session made or prepared by the other user or coach. In addition to an individual training session, it is naturally also possible to download a training programme of several days, weeks, or a year.

In one embodiment of the device, the user transfers the already accumulated EPOC or training effect wirelessly or using a memory card or similar from a gym device or similar to another when changing devices, so that the training on the new device can continue from where it ended on the other device. In one application, the EPOC accumulated during the training session of the members of a training group is transferred wirelessly to a computer, from where the coach of the group can use a monitor to check the accumulation of exercise and adjust the rate of the training for either the whole group or for individuals.

Operating Example 2

Monitoring of a Training State

Figure 5A:
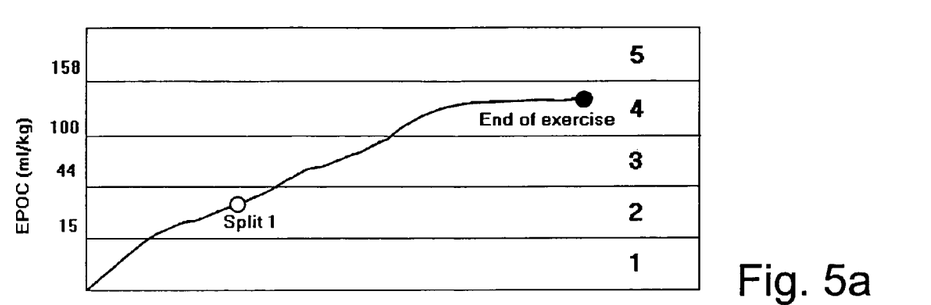
FIGS. 5a and 5b show the physiological progress of training in one training session without a precise target.
Figure 5B:
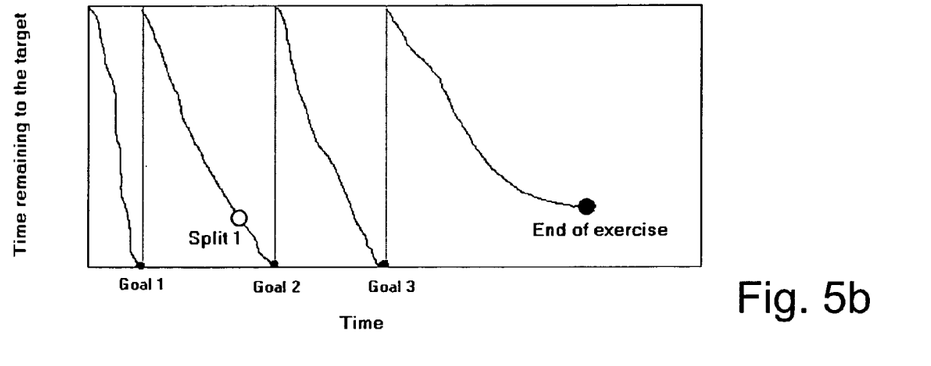

FIGS. 5a-5b show the accumulation of EPOC during training. In the example of the figures, the user has not set a training target, in what case the user is shown the EPOC/time to the following training effect level. The lower image in FIG. 1 illustrates the operation of the time calculators towards the training-effect limits.

Figure 5C:
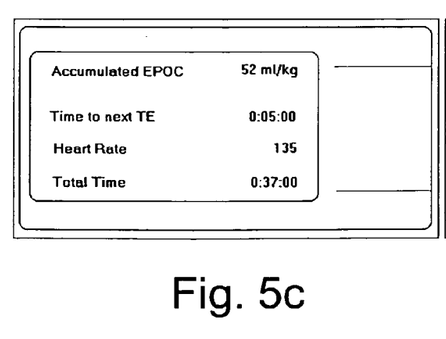
Figure 5D:
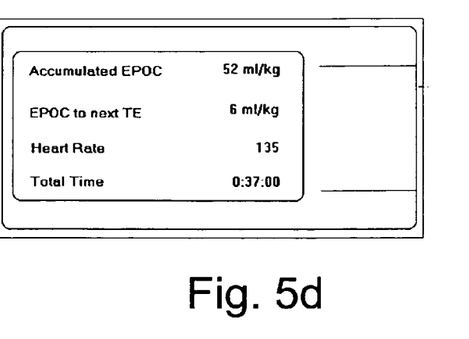

FIGS. 5c-5d show the information visible to the user from the monitor from the 'SPLIT' point of FIG. 1.

Operating Example 3

Achievement of a Set Target State

Figure 6A:
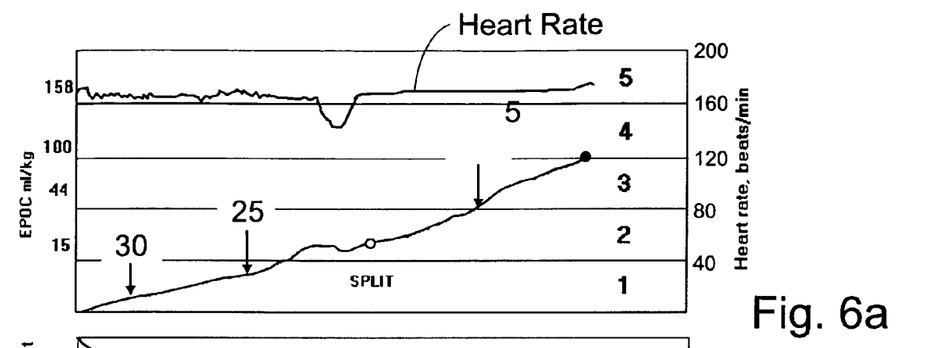
FIGS. 6a and 6b show the physiological progress of training in a second training session with a precise target.
Figure 6B:
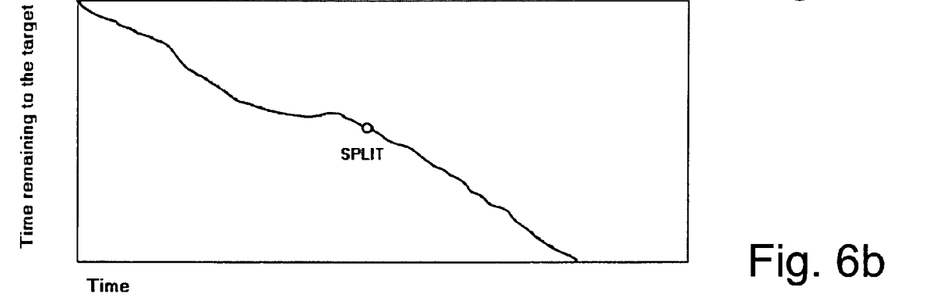

FIGS. 6a-6b: the training targets can be set as an EPOC value or as a training effect (TE number). In the upper image, the accumulation of the EPOC is shown graphically towards the target state (TE 4) set by the user. The grey balls in the image shown the remaining time in minutes to the achievement of the target state. The lower image shows the operation of the time counter.

Figure 6C:
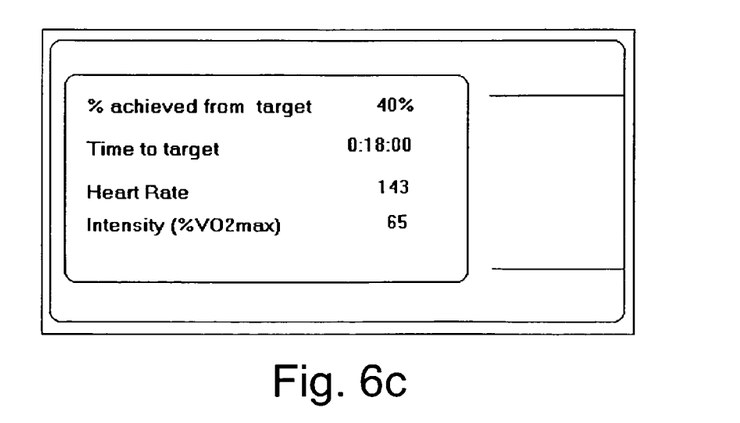

FIG. 6c shows the information visible in the monitor to the user from the 'SPLIT' point of FIG. 6a. The degree of reaching the target state can be shown as a percentage, the remaining EPOC reading, or the remaining time.

Operating Example 4

Setting the Time and EPOC Targets

Figure 7:
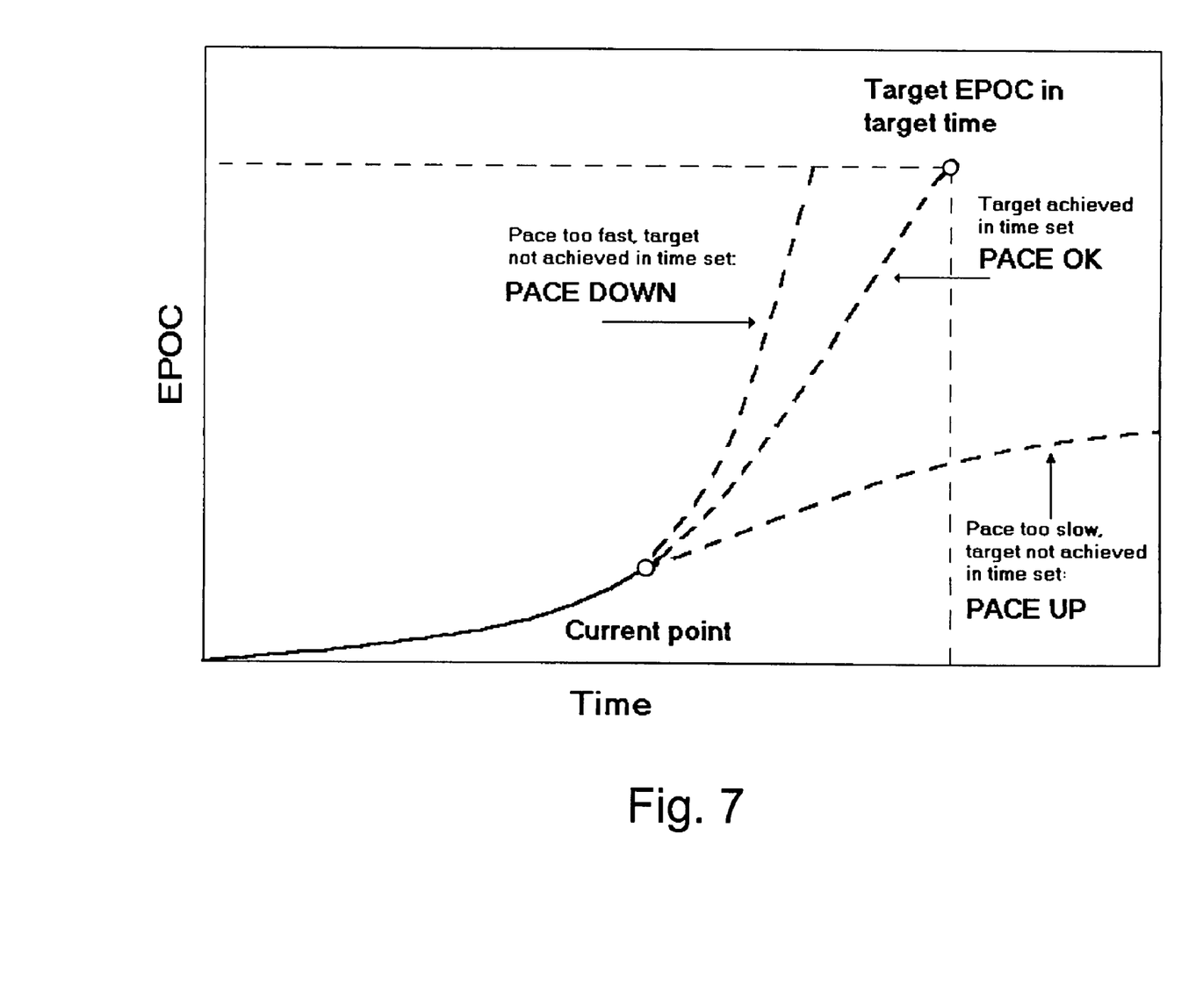
FIG. 7 shows the progress of training using various parameters.

According to FIG. 7, the training targets can be set to be time dependant. In the example of FIG. 7, it is wished to reach a specific EPOC in a certain time. 'Current point' shows the stage of the training at which a certain amount of EPOC has already accumulated. The program calculates the optimal exertion for the user so that the target can be achieved in the set time. The optimal intensity is calculated with the aid of the accumulated EPOC, the remaining time, and the EPOC difference (target state): if these three are known, the fourth can be calculated. If the EPOC accumulation is optimal, the meter shows 'PACE OK'. If the intensity of the performance is too light or too hard, the user is guided with the comments 'PACE UP' or 'PACE DOWN'. Alternatively it is possible to give directly a precise intensity value.

Operating Example 5

Recovery

Figure 8A:
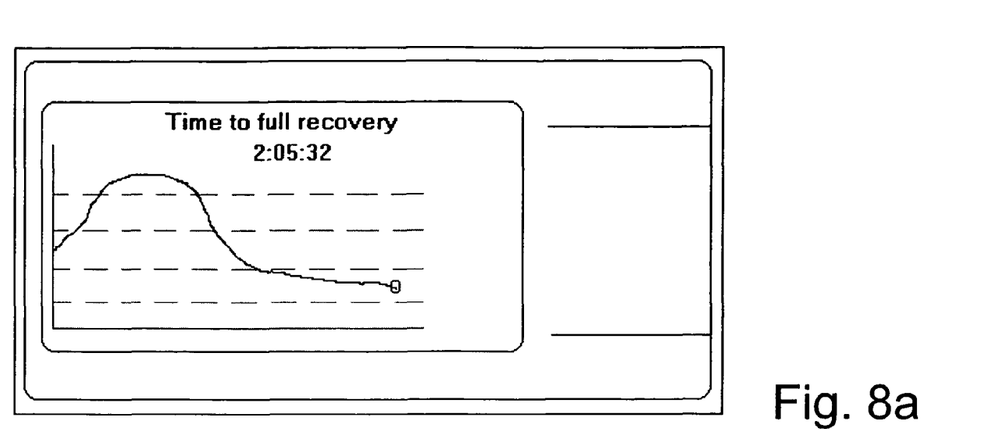
FIGS. 8a and 8b show the physiological progress of the recovery stage and the display of such a state.
Figure 8B:
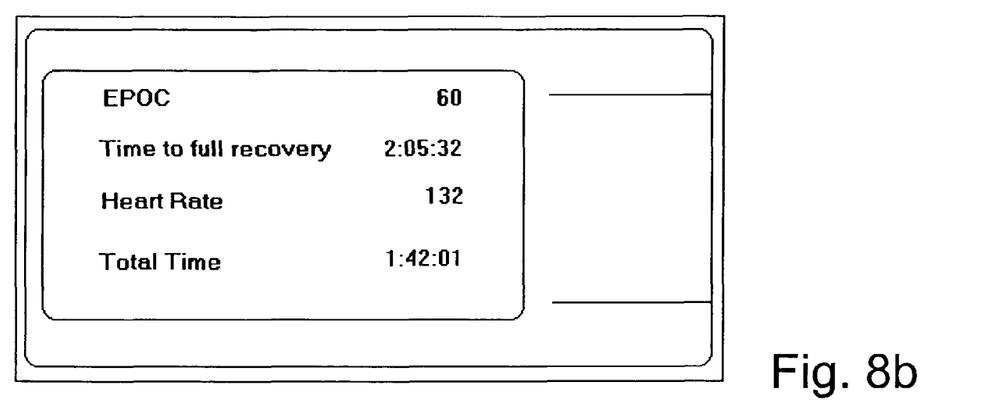

FIGS. 8a-8b: after a hard training session, the recovery function of the program can be used to show the remaining EPOC and time to a full recovery. In FIG. 8a, the recovery is shown graphically while FIG. 8b shows numerically the momentary information visible to the user from the monitor.

Operating Example 6

Guided Interval Training

Figure 9:
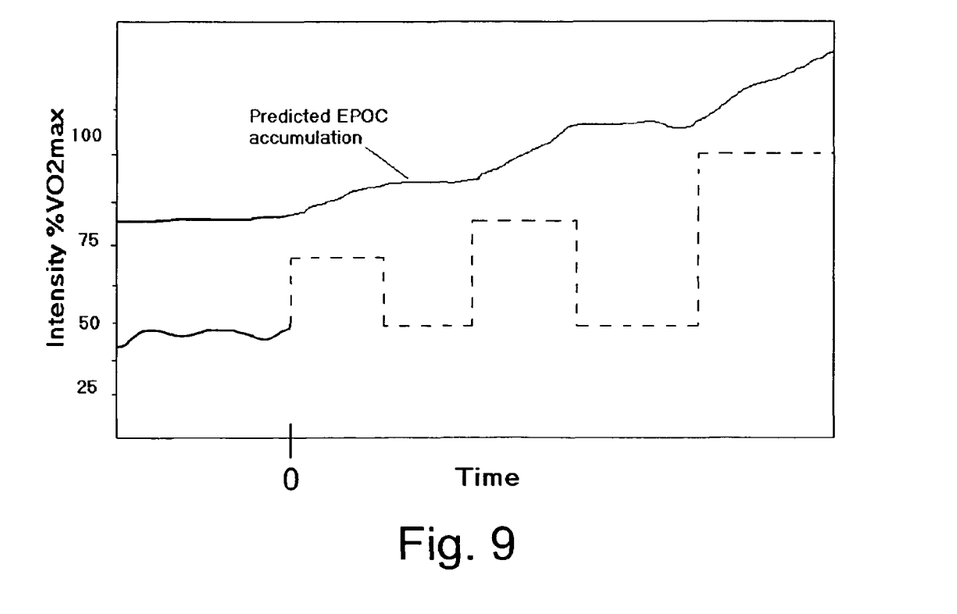
FIG. 9 shows training with an intensity that changes in steps.
Figure 10A:
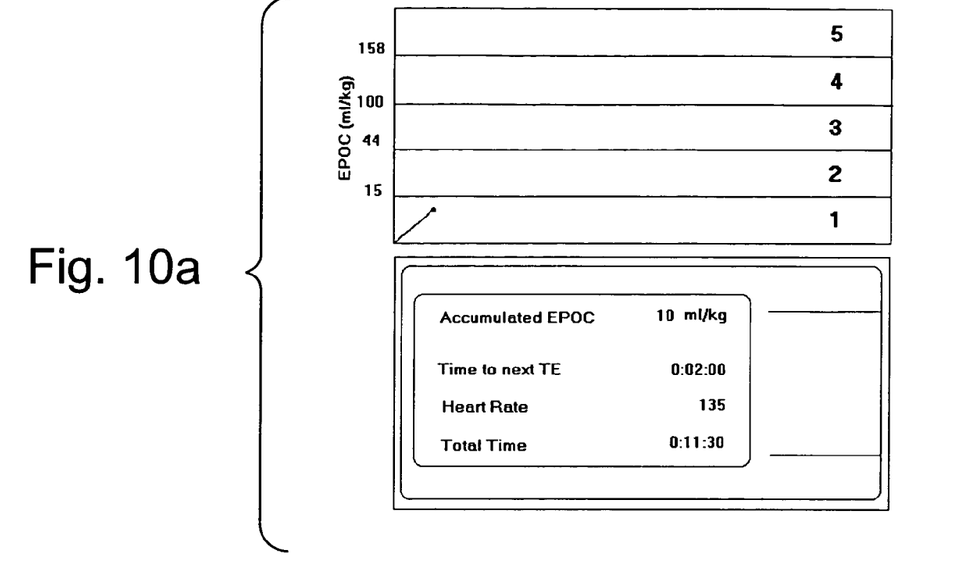
FIGS. 10a-10d show the progress physiologically of one training session and a display in the recovery stage.
Figure 10B:
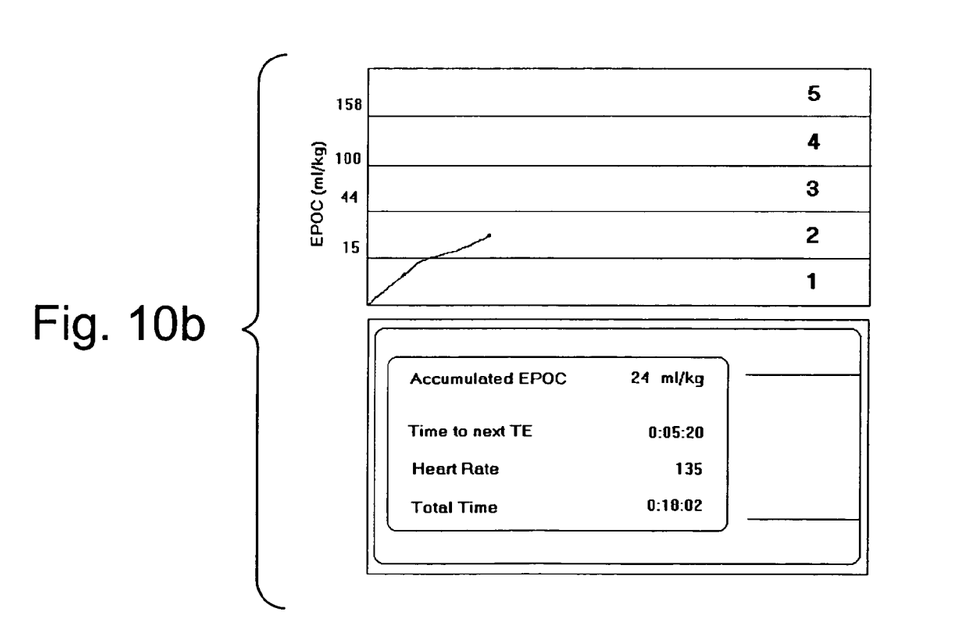
Figure 10C:
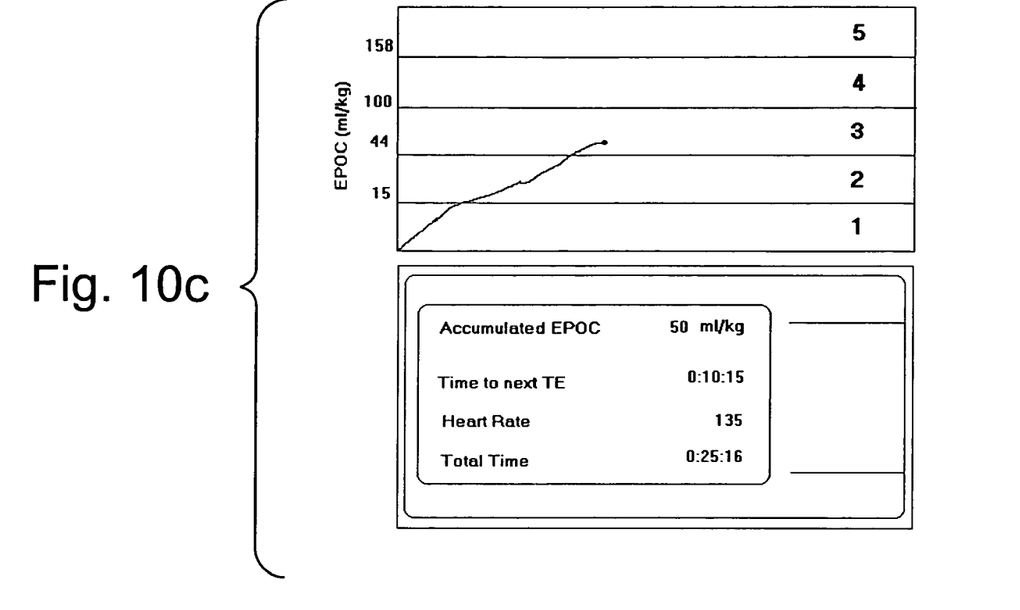
Figure 10D:
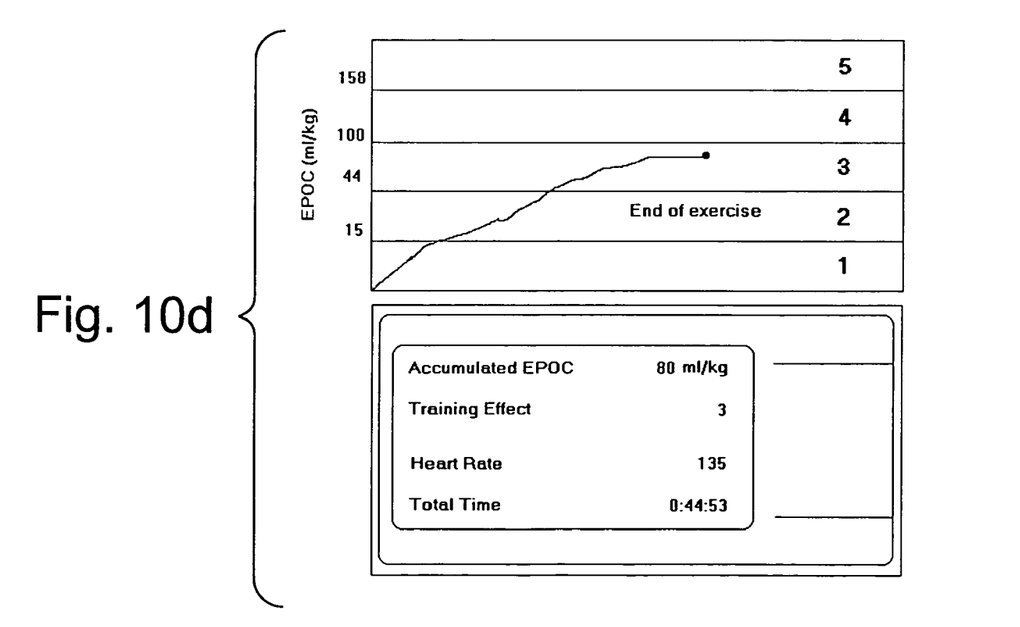

In FIG. 9 is an example of an interval-training application for using in exercise devices (e.g., a cycle ergometer). At first the user sets the desired training target for themselves. The loading of an interval-training session is affected by the activity class, the set training target, and the initial warm-up EPOC-number/heart rate (the lower solid line in the image). The upper solid line shows the predicted EPOC accumulation towards the target. The exercise steps of the interval-training session (exertion and duration, number of loading steps) and the recovery times between the series can also be set manually. According to this example, the planned future intensity is not necessarily a constant, but should instead be stepped.

FIGS. 10a-10d show graphs and a corresponding display of the EPOC accumulation from the same training session at different points in time. In this case, a training target is not given, so that the user is shown the time to the achieving of the following training effect level.

REFERENCES

ACSM—American College of Sports Medicine. (2001). ACSM's Guidelines for Exercise Testing and Prescription. Philadelphia: Lippincot Williams & Wilkins.

Brooks, G. A, & Fahey, T. D. (1984). Exercise Physiology. Human Bioenergetics and its Applications. New York: Macmillan Publishing Company.

Rusko, H. (Ed.) (2003). Handbook of Sports Medicine and Science—Cross Country Skiing. Blackwell Science.

The invention claimed is:

1. A system for monitoring a cumulative physiological state and for predicting a target state under physical exercise, wherein the user's physiological state is defined by a EPOC (excess post-exercise oxygen consumption) value as a cumulative physiological variable indicating achieved training effect and the target state defines a respective value of the cumulative physiological variable after an exercise having a total duration, said system including:
   means for measuring time,
   means for measuring intensity of the exercise at each moment to obtain a measured intensity and for registering the measured intensity relative to time, and
   a control unit connected to said means for measuring time and said means for measuring and registering intensity, the control unit further comprising:
      a user-interface device, including an input device for selecting an output variable and for entering the values of initial variables before the exercise, and an output device for displaying the output variable, the output variable being one of the following three variables: said target state, intensity of future exercise, and duration of remaining exercise; the two other variables being entered by the user as said initial variables,
      first software means for calculating the current EPOC value during the exercise, with the aid of the measured intensity of exercise and the preceding current EPOC value, and
      second software means for calculating the output variable during the exercise using a mutual relationship between the current EPOC value and two variables of said three variables,
         wherein the system is arranged to calculate and display the value of the output variable using the output device, in real time and continuously.

2. A system according to claim 1, wherein the output device consists of a display.

3. A system according to claim 1, wherein the output device consists of graphical display means for showing graphically the development of the exercise state.

4. A system according to claim 1, wherein the system includes an exercise device, in which said control unit is located.

5. A system according to claim 1, wherein the output device includes voice-synthesis and audio means for presenting the output variable as a voice message.

6. A system according to claim 1, wherein the system includes a mobile station, in which the control unit is located.

7. A system according to claim 1, wherein the means for measuring the variable defining the intensity of the exercise at each moment includes a measuring device for measuring one or more variables from the following group: external power, motion, energy consumption, heart rate, oxygen consumption, respiration rate, or heat flow from the surface of the skin.

8. A system according to claim 1, wherein the system includes a wristop device, in which said control unit is located.

9. A system according to claim 1, wherein said second software means is arranged to simulate the cumulative physiological variable using the initial variables and varied output variables, until the initial variables are realized.

10. A system according to claim 1, wherein the training effect is determined on basis of EPOC peak value.

\* \* \* \* \*